(12) United States Patent
Doble

(10) Patent No.: US 6,280,459 B1
(45) Date of Patent: Aug. 28, 2001

(54) BACK BITING SURGICAL INSTRUMENT

(76) Inventor: Peter Doble, 3399 Willon Way, Twin Falls, ID (US) 83308

( * ) Notice: Subject to any disclaimer, the term of this patent is extended or adjusted under 35 U.S.C. 154(b) by 0 days.

(21) Appl. No.: 09/446,258

(22) PCT Filed: Aug. 31, 1998

(86) PCT No.: PCT/US98/18075

§ 371 Date: Dec. 20, 1999

§ 102(e) Date: Dec. 20, 1999

(87) PCT Pub. No.: WO99/11183

PCT Pub. Date: Mar. 11, 1999

Related U.S. Application Data

(60) Provisional application No. 60/057,467, filed on Sep. 3, 1997.

(51) Int. Cl.[7] .................................................. A61B 17/32
(52) U.S. Cl. ............................................. 606/206; 606/170
(58) Field of Search ................................... 606/205, 206, 606/207, 208, 170, 174, 184

(56) References Cited

U.S. PATENT DOCUMENTS 5,569,299 * 10/1996 Dill et al. ............................. 606/207
5,618,306 * 4/1997 Roth et al. ........................... 606/205
5,683,359 * 11/1997 Farkas et al. ........................ 606/170

* cited by examiner

*Primary Examiner*—Gary Jackson
*Assistant Examiner*—Kevin Truong
(74) *Attorney, Agent, or Firm*—Barnes & Thornburg

(57) ABSTRACT

A surgical instrument (10) is provided for cutting tissue. The surgical instrument (10) includes a shaft (20) having proximal (84) and distal (40) ends, a cutter (12) coupled to the distal end (40), and a handle (16) coupled to the proximal end (84). The cutter (12) is formed to include a base (30) having two cutting edges (50) providing an opening (51), a slider (32), and a tip (34) coupled to both the base (30) and the slider (32). The cutter (12) is formed to move between a fully open position in which the cutting edges (50) of the tip (34) form an obtuse angle (124) relative to the shaft (20) and a fully closed position in which the tip (34) is received within the opening (51) of the base (30). The handle (16) is arranged to move the cutter (12) between the open and closed positions.

50 Claims, 6 Drawing Sheets

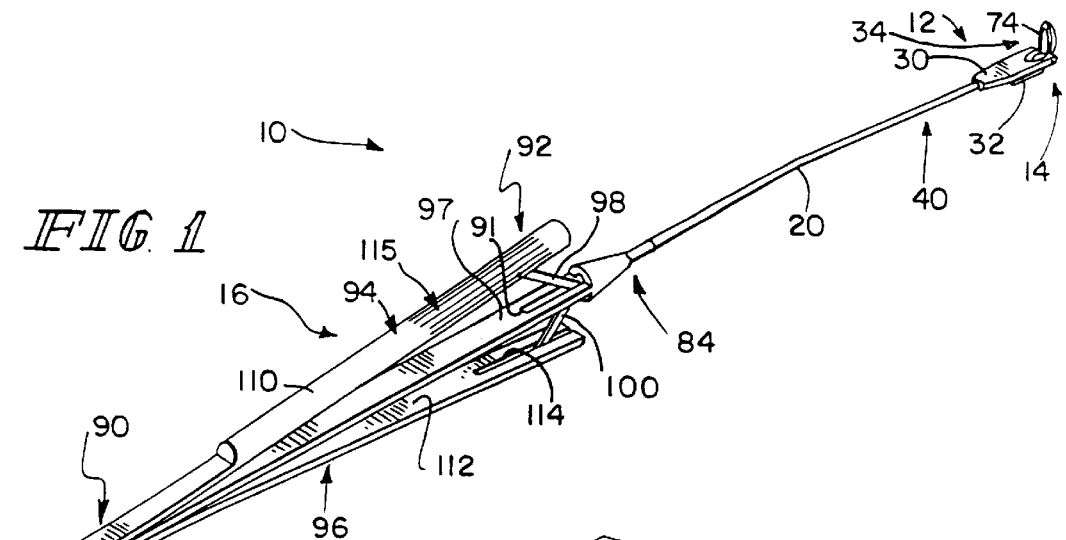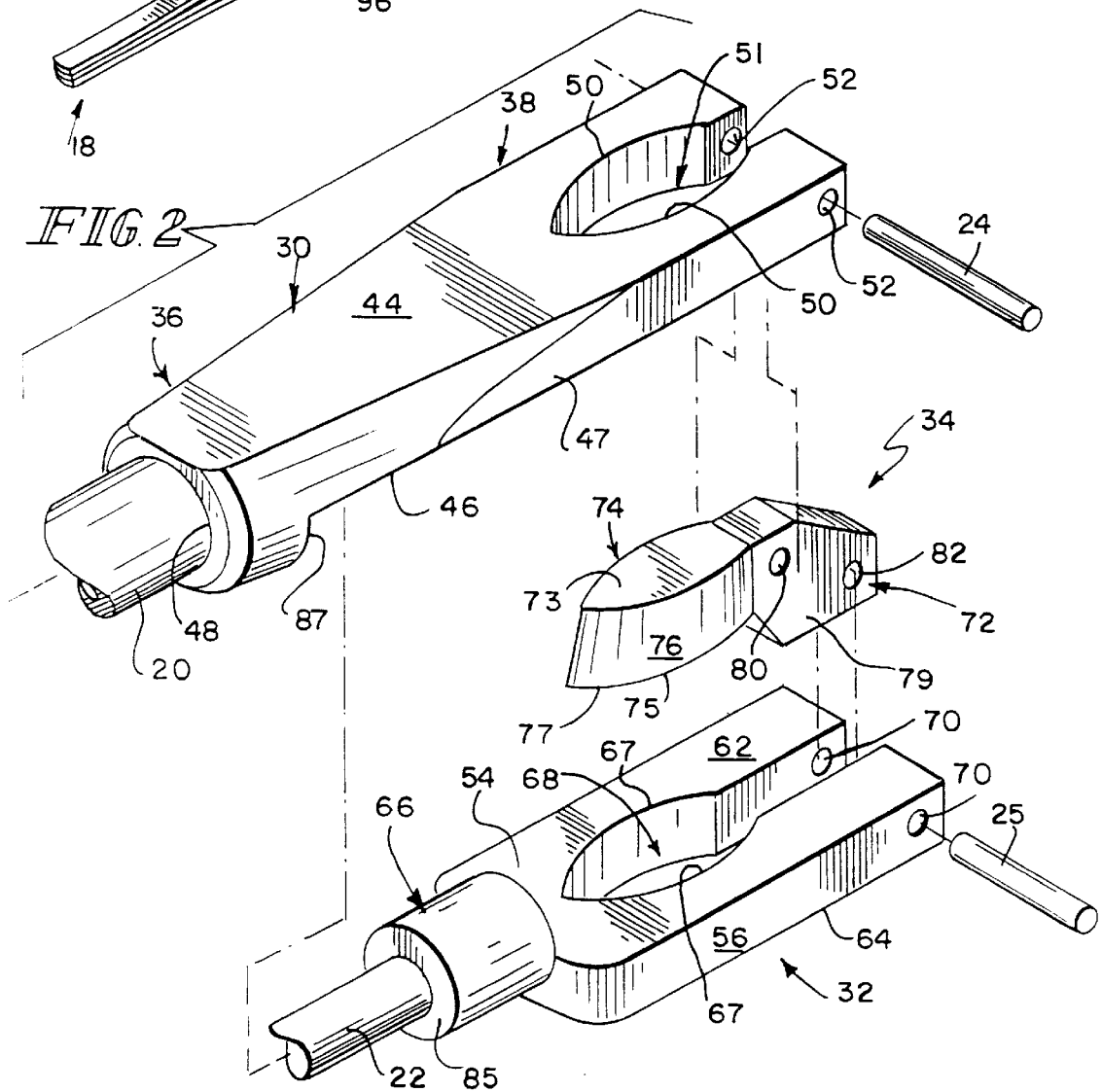

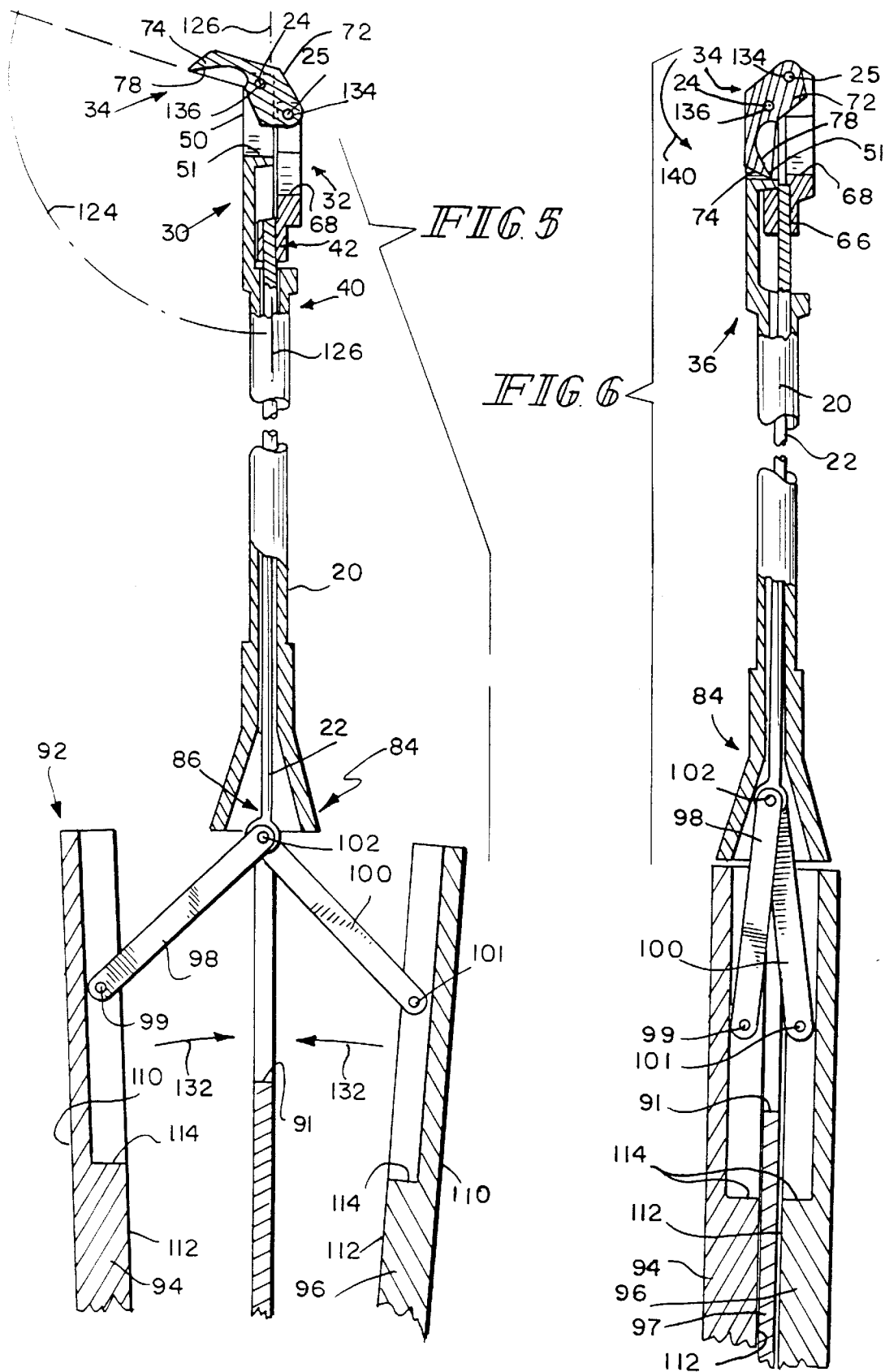

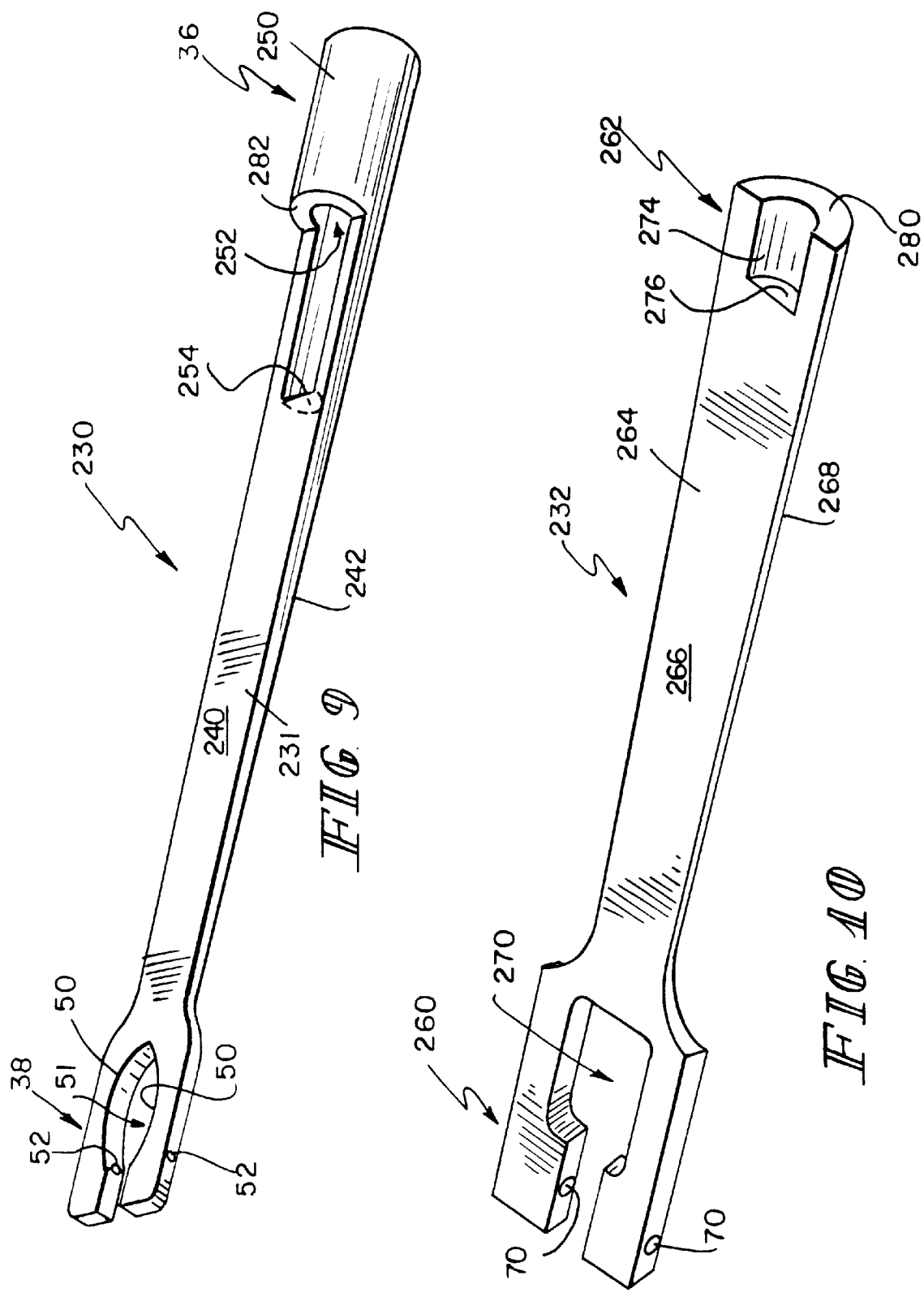

US 6,280,459 B1

BACK BITING SURGICAL INSTRUMENT

CROSS-REFERENCE TO RELATED APPLICATIONS

This application is a U.S. national application of international application Ser. No. PCT/US98/18075 filed Aug. 31, 1998, which claims priority to U.S. provisional application Ser. No. 60/057,467 filed Sep. 3, 1997.

BACKGROUND AND SUMMARY OF THE INVENTION

The present invention relates to surgical instruments, and particularly to surgical instruments used in minimally invasive endoscopic transitional space surgeries or other endoscopic procedures. More particularly, the present invention relates to a surgical instrument used for cutting tissue.

During most minimally invasive surgeries of the sinuses, knee, shoulder, and other joints, a smaller surgical instrument is preferred. A number of instruments have been developed, including those shown in U.S. Pat. Nos. 5,443,475 and 4,977,900, for such surgeries. The disclosure of these patents is incorporated herein by reference for purposes of combining techniques and concepts. Instruments such as those shown in these referenced patents are typically used with an endoscope which allows the surgeon to view the interior of the area under repair through an eye piece or, alternatively, on a video display screen.

An initial process in many minimally invasive endoscopic transitional space (sinus) surgeries is cutting the uncinate process. The uncinate process is an obstructive piece of cartilage and is cut for the purpose of exposing the ostium, which leads into the maxillary sinus cavity. A large degree of precision, maneuverability, and control is needed in order to effectively cut the uncinate process and many other tissues in endoscopic surgeries.

According to the present invention, a surgical instrument is provided for cutting tissue. The instrument includes a shaft having distal and proximal ends and a cutter coupled to the distal end of the shaft. The cutter is formed to include a base, a slider positioned to lie adjacent to the base, and a tip coupled to the base and the slider. The base is formed to include an aperture providing two cutting edges and the tip is also formed to include two corresponding cutting edges for cooperation with the cutting edges of the base. The cutter is formed to move between a filly open position in which the cutting edges of the tip form an obtuse angle relative to the shaft to a fully closed position in which the tip is received within the aperture of the base. The instrument is also formed to include a handle coupled to the proximal end of the shaft. The handle is arranged to move the cutter between open and closed positions.

In preferred embodiments, the handle is formed to include a right handle grip, a left handle grip, and a center beam positioned to lie between the right and left handle grips. The right and left handle grips are coupled to the center beam at a proximal end of the handle and are normally spaced-apart from the center beam at a distal end of the handle. In order to move the cutter to the fully closed position, the handle grips are squeezed toward the center beam in a direction transverse to an axis running through the shaft. The surgical instrument of the present invention is adapted to be held by the thumb and index finger, supported on the middle finger and actuated by squeezing the thumb and index finger together.

Additional features and advantages of the invention will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which:

FIG. 1 is a perspective view of a back biting surgical instrument of the present invention showing a cutter for cutting tissue during an endoscopic procedure, a handle for moving the cutter between fully opened and fully closed positions, and a hollow shaft extending between the cutter and the handle;

FIG. 2 is an exploded perspective view of the cutter of the present invention showing a base having two curved cutting edges forming an opening, a slider also having two curved edges forming an opening, and a tip having a cutter head including two curved cutting surfaces adapted to cooperate with the cutting edges of the base to create a shearing motion;

FIG. 5 is a sectional view, with portions broken away, of the cutter in the fully open position showing an obtuse angle formed between the lower surface of the cutter head and an axis running through a distal end of the shaft and also showing the handle including two handle grips, a link pivotally coupled to each handle grip and a rod received within the hollow shaft, and a center beam positioned to lie between each handle grip;

FIG. 6 is a sectional view similar to FIG. 5 showing the cutter in the fully closed position so that the handle grips are moved inward toward the center beam and the cutter head of the tip is received within the opening of the base;

FIG. 9 is a perspective view of the alternate base of FIG. 8 showing an elongated mid-section and a semi-circular portion with a cut-out section at a proximal end; and FIG. 10 is a perspective view of the alternate slider of FIG. 8 showing a rectangular shaped opening and a groove at a proximal end for receiving the rod.

DETAILED DESCRIPTION OF THE DRAWINGS

Figure 3:
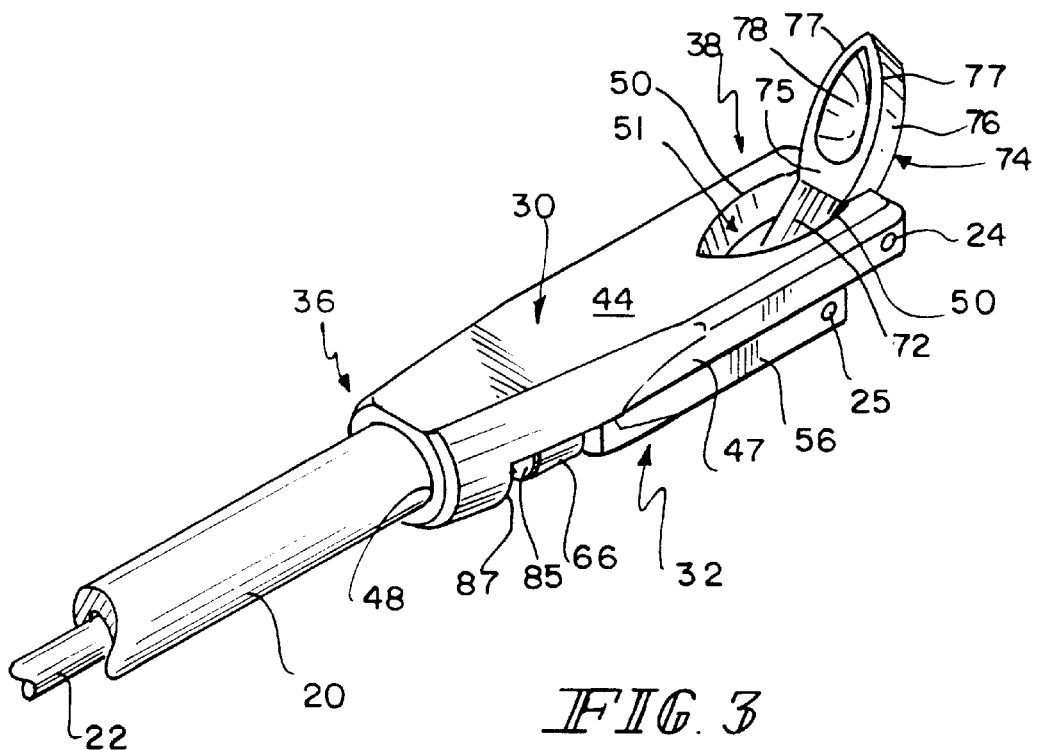
FIG. 3 is a perspective view of the cutter in the fully open position showing the cutting edges of the cutter head, a recessed portion of a lower of the cutter head, and also showing the tip being pivotally coupled to each of the base and the slider.

A surgical instrument 10 is provided for use in minimally invasive endoscopic transitional space surgeries (sinus surgeries), but may be used for other endoscopic procedures as well. Instrument 10 is formed to include a cutter 12 located at a distal end 14, a handle 16 located at a proximal end 18, a hollow shaft 20, and a rod 22 received within hollow shaft 20. The hollow shaft 20 and rod 22 each extend between cutter 12 and handle 16, as shown in FIG. 1. The cutter 12 is formed to move between a fully open position and a fully closed position through operation of the handle 16. Handle 16 is formed to be held by a surgeon or technician by using a "pencil-like" grip, as shown in FIG. 10.

Cutter 12 is formed to include a base 30, a slider 32, and a tip 34 coupled to both base 30 and slider 32, as shown by the dotted lines in FIG. 2. Base 30 is formed to include a proximal end 36 and a distal end 38. Proximal end 36 is coupled to a distal end 40 of shaft 20. Base 30 is also formed to include a top surface 44, a bottom surface 46, and side walls 47. Proximal end 36 of base 30 is formed to include a shaft-receiving aperture 48 and distal end 38 is formed to include two cutting edges 50 forming a tear-drop shaped opening 51 extending through distal end 38 of base 30. Apertures 52 are formed to extend through distal end 38 and are provided for receiving a first pin 24 in order to pivotally couple tip 34 with base 30.

Figure 4:
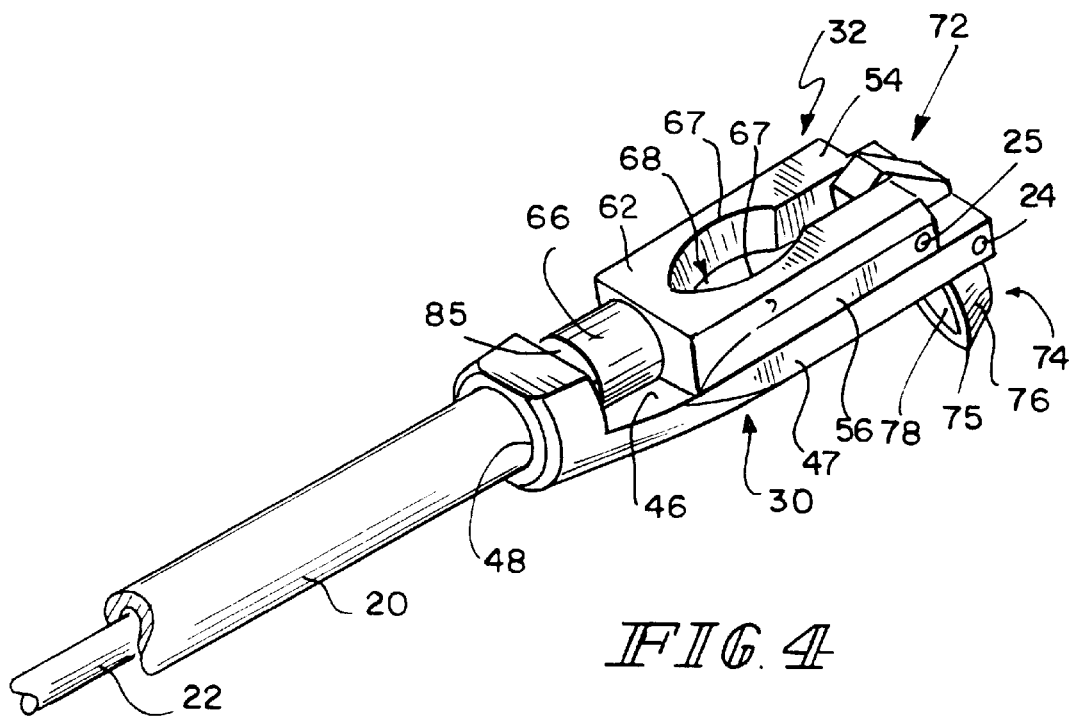
FIG. 4 is a perspective view a the backside of the cutter in the fully open position showing the opening of the slider.

Slider 32 is formed to include a body 54 having side walls 56, a top surface 62, and a bottom surface 64 where side walls 56 extend between top and bottom surfaces 62, 64. Body 54 is also formed to include two curved edges 67 forming a tear-drop shaped opening 68 similar to opening 51 of base 30 and apertures 70 extending through body 54 and provided for receiving a second pin 25 in order to pivotally couple tip 34 with slider 32. Slider 32 is also formed to include a hollow cylinder 66 coupled to body 54 and formed for receiving a distal end 42 of rod 22. When fully assembled, top surface 62 of slider 32 is positioned to lie adjacent to and in engagement with bottom surface 46 of base 30, as shown in FIGS. 3 and 4.

Tip 34 is formed to include a pivot head 72 and a cutter head 74 extending from pivot head 72. Cutter head 74 is tear-drop shaped and is formed to include an upper surface 73, a lower surface 75, and two curved side surfaces 76 extending between upper and lower surfaces 73, 75. Two cutting edges 77, as shown in FIG. 3 define an outer perimeter of lower surface 75. Cutting edges 77 of cutter head 74 are formed to cooperate with cutting edges 50 of base 30. Lower surface 75 is also formed to include a recessed portion 78, also shown in FIG. 3. Pivot head 72 of tip 34 is formed to include two side walls 79, a first aperture 80 formed to extend between side walls 79, and a second aperture 82 also formed to extend between side walls 79. When assembled, pivot head 72 of tip 34 is received within opening 51 of base 30 and opening 68 of slider 32 so that first aperture 80 is positioned to align with apertures 52 of base 30 and second aperture 82 is positioned to align with apertures 70 of slider 32. Aperture 80 and apertures 52 receive first pin 24 therethrough in order to pivotally couple tip 34 to base 30. Aperture 82 and apertures 70 are formed to receive second pin 25 in order to pivotally couple tip 34 to slider 32.

Figure 7:
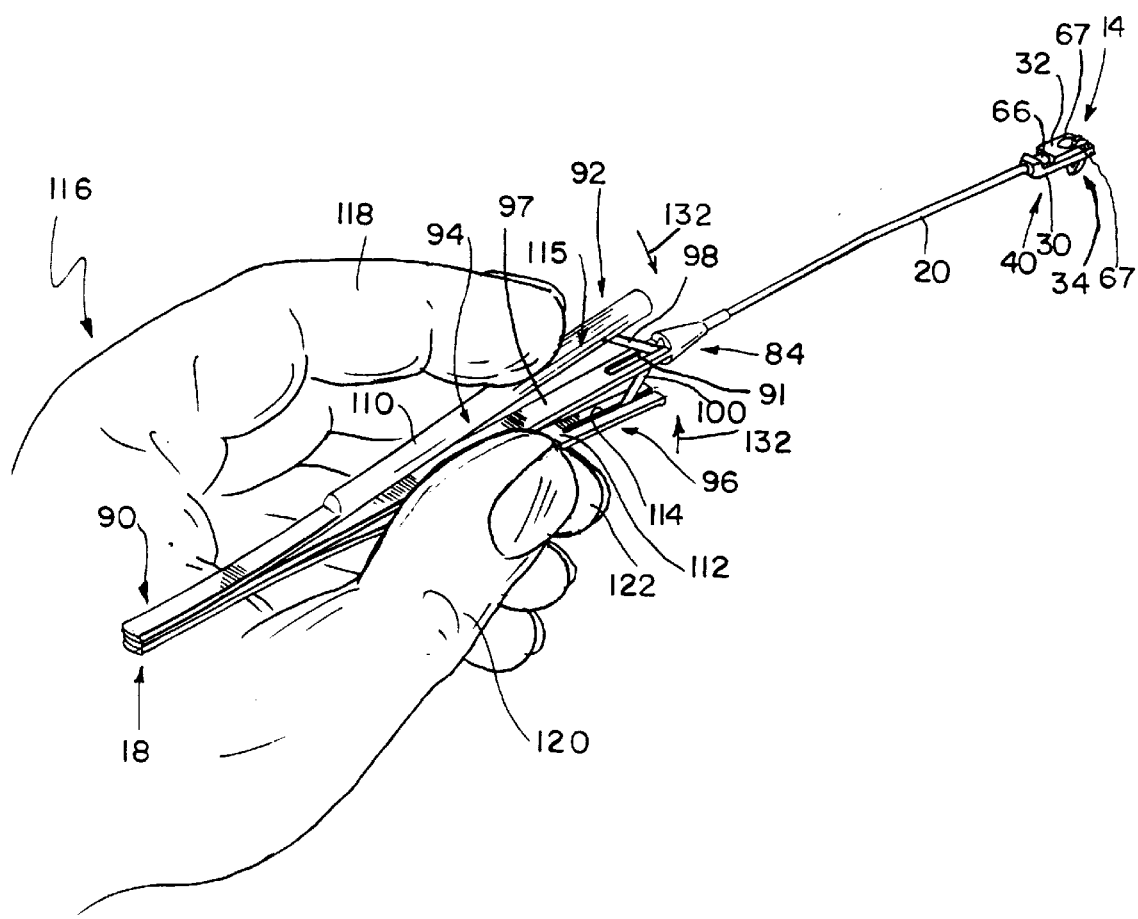
FIG. 7 is a perspective view of the surgical instrument of the present invention showing a hand grasping the handle of the present invention with a "pencil-like" grip for improved control and precision in operation.

Shaft 20 and rod 22 are each formed to include distal ends 40, 42, respectively, and a proximal end 84, 86, respectively, as shown in FIG. 7. Shaft 20 is hollow so that rod 22 is received within shaft 20 and is movable relative to shaft 20. Distal end 40 of shaft 20 is received within shaft-receiving aperture 48 of base 30. Proximal end 84 of shaft 20 is coupled to handle 16. Distal end 42 of rod 22 is received within cylinder 66 of slider 32. Similar to shaft 20, proximal end 86 of rod 22 is coupled to handle 16. In the fully open position, a lower surface 85 of hollow cylinder 66 of slider 32 is positioned to engage an upper surface 87 of proximal end 36 of base 30, as shown in FIG. 4. In the fully closed position, as shown in FIG. 6, lower surface 85 is spaced-apart from upper surface 87. Although base 30 and shaft 20 are shown and described as two separate members, it is within the scope of the present invention to manufacture base 30 and shaft 20 as one integral part (not shown). Slider 32 and rod 22 are also shown and described as two separate members, however, it is within the scope of the invention to also combine slider 32 and rod 22 to form one integral part (not shown).

Referring now to FIGS. 1, 5, 6, and 7, handle 16 is formed to include a proximal end 90, a distal end 92, a left handle grip 94, a right handle grip 96, a center beam 97 positioned to lie between left and right handle grips 94, 96, and a first and second link 98, 100. Handle grips 94, 96 are each welded to center beam 97 at proximal end 90 and are spaced-apart from center beam 97 at distal end 92. It is within the scope of the present invention, however, to include any number of means of coupling each handle grip 94, 96 to center beam 97 at proximal end 90. Each handle grip 94, 96 is formed to include a curved outer surface 110 and a flat inner surface 112 positioned to face center beam 97. Flat inner surface 112 of each handle grip 94, 96 is formed to include an inner slit 114 at distal end 92. Inner slit 114 is formed to extend only partially through each handle grip 94, 96. Curved outer surface 110 of each handle grip 94, 96 is formed to include a splined portion 115 in order to make handle 16 easy for a user 116 to grasp, as shown in FIG. 7. Although splined portion 115 is shown, it is within the scope of the present invention to include handle grips 94, 96 having outer surface 110 including any type of knurled, textured, or ridged portion. Proximal end 84 of shaft 20 is coupled to center beam 97, as shown in FIG. 1. Shaft 20 and center beam 97 may also be manufactured as one integral part.

First link 98 is received within inner slit 114 of left handle grip 94 and is coupled therein at a pivot point 99. Second link 100 is similarly received within inner slit 114 of right handle grip 96 and is coupled therein at a pivot point 101. Each link 98, 100 is also coupled to proximal end 86 of rod 22 at a pivot point 102. Distal end 92 of center beam 97 is coupled to proximal end 84 of shaft 20, as shown in FIGS. 1 and 7. Distal end 92 of center beam 97 is also formed to include a cut-out portion 91 and pivot point 102 is positioned to lie within cut-out portion 91. Cut-out portion 91 of center beam 97 also provides a space in which links 98, 100 to can move during operation.

Although handle 16 may be held in a number of ways, it is preferred for user 116 to grasp handle 16 with a "pencil-like" grip, as shown in FIG. 7. With the pencil-like grip, an index finger 118 of user 116 is placed on the splined portion 115 of either one of the handle grips 94, 96. A thumb 120 of the user 116 is place in contact with the splined portion 115 of the other handle grip 94, 96 so that surgical instrument 10 is supported between index finger 118 and thumb 120. A middle finger 122 of the user 116 is positioned to engage the same one of the handle grips 94, 96 which is supported by thumb 120 so that surgical instrument 10 may be better supported providing user 116 with increased control during surgical operations. Instrument 10 may be held, as shown in FIG. 7, with the cutter head 74 of tip 34 facing downward, or instrument 10 may be held so that the cutter head 74 faces upward.

Cutter 12 may be moved between the fully open position, as shown in FIG. 5, in which an obtuse angle 124 is created between the lower surface 75 of cutter head 74 and an axis 126 running parallel to distal end 40 of shaft 20 and the fully closed position, as shown in FIG. 6, where cutter head 74 is received within opening 51 of base 30. In the fully closed position, inner surface 112 of each handle grip 94, 96 is positioned to lie adjacent to and in engagement with center beam 97. During the motion between the fully open position and the fully closed position, cutting edges 77 and side surfaces 76 of cutter head 74 are positioned to engage cutting edges 50 forming opening 51 within base 30, thus creating a shearing action between cutting edges 77 and surfaces 66 of cutter head 74 and cutting edges 50 of base 30. The two sets of cutting edges 50, 77 cooperate with each other in order to form the shearing action.

In operation, user 116 holds handle 16 using the pencil-like grip described above. With index finger 118 and thumb 120, user 116 urges each handle grip 94, 96 inward in a direction 132, as shown by the arrows in FIG. 5. Left and right handle grips 94, 96 are urged to move toward center beam 97 until inner surface 112 of each handle grip 94, 96 is positioned to lie adjacent to and in engagement with center beam 97, as shown in FIG. 6. The handle 16 is thus operable in a "tweezer-like" fashion.

First and second links 98, 100 are coupled to respective handle grips 94, 96 at pivot points 99, 101 located within slits 114. As handle grips 94, 96 are urged in direction 132 toward center beam 97, first and second links 98, 100 are urged to pivot about pivot points 99, 101 so that first and second links 98, 100 are urged to move toward a generally upright or vertical position parallel to center beam 97. The inward and upward movement of links 98, 100 causes links 98, 100 to also pivot about pivot point 102 and thus move pivot point 102 upward as well. Because links 98, 100 are coupled to rod 22 at pivot point 102, rod 22 is also urged to move upward within shaft 20. During this motion, shaft 20 and beam 97 remain stationary relative to handle grips 94, 96, links 98, 100, and rod 22.

Distal end 42 of rod 22 is received within cylinder 66 of slider 32. Distal end 42 of rod 22 is thus coupled to slider 32 so that as rod 22 is moved upward, due to the inward, closing motion of handle grips 94, 96, rod 22 urges slider 32 in the same upward direction, as shown in FIG. 6. Slider 32 is coupled to pivot head 72 at a pivot point 134 by second pin 25. As slider 32 is moved upward, second pin 25 and pivot point 134 are also moved upward. As shown in FIG. 6, when cutter 12 is in the fully closed position, opening 68 of slider 32 is positioned to align with opening 51 of base 30 in order to allow cut tissue to pass therethrough.

Pivot head 72 is coupled to base 30 by first pin 24 at a pivot point 136. Because base 30 remains stationary as slider 32 moves upward relative to shaft 20, tip 34 is urged to pivot about both pivot points 134, 136 causing tip 34 to pivot in a downward direction, as shown by arrow 140 in FIG. 6. In the fully open position, as shown in FIG. 5, first pin 24 and pivot point 136 are positioned to lie generally above second pin 25 and corresponding pivot point 134. In the fully closed position, however, first pin 24 and pivot point 136 are positioned to lie generally below second pin 25 and pivot point 134. This is due to the upward motion of rod 22 causing pivot point 134 to move upward while pivot point 136 remains stationary with base 30.

As cutter 12 is moved toward the fully closed position, side surfaces 76 and cutting edges 77 of cutter head 74 are urged to pass through opening 51 formed by cooperating cutting edges 50 of base 30. As cutting edges 77 and side surfaces 76 of cutter head 74 pass through opening 51, a shearing action is created between the two cutting edges 77, 50. When used in surgery, for endoscopic surgical procedures such as sinus surgeries, this shearing action operates to cut away tissue from the surgical site. The cut tissue (not shown) is received within recessed portion 78 of cutter head 74. Because tear-drop shaped opening 68 of slider 32 is positioned to align with opening 51 of base 30 when cutter 12 is in the fully closed position, the tissue which is cut from the surgery site and received within recessed portion 78 is able to be passed through openings 51, 68 for disposal in order to avoid the clogging of instrument 10 with tissues and debris.

Figure 8:
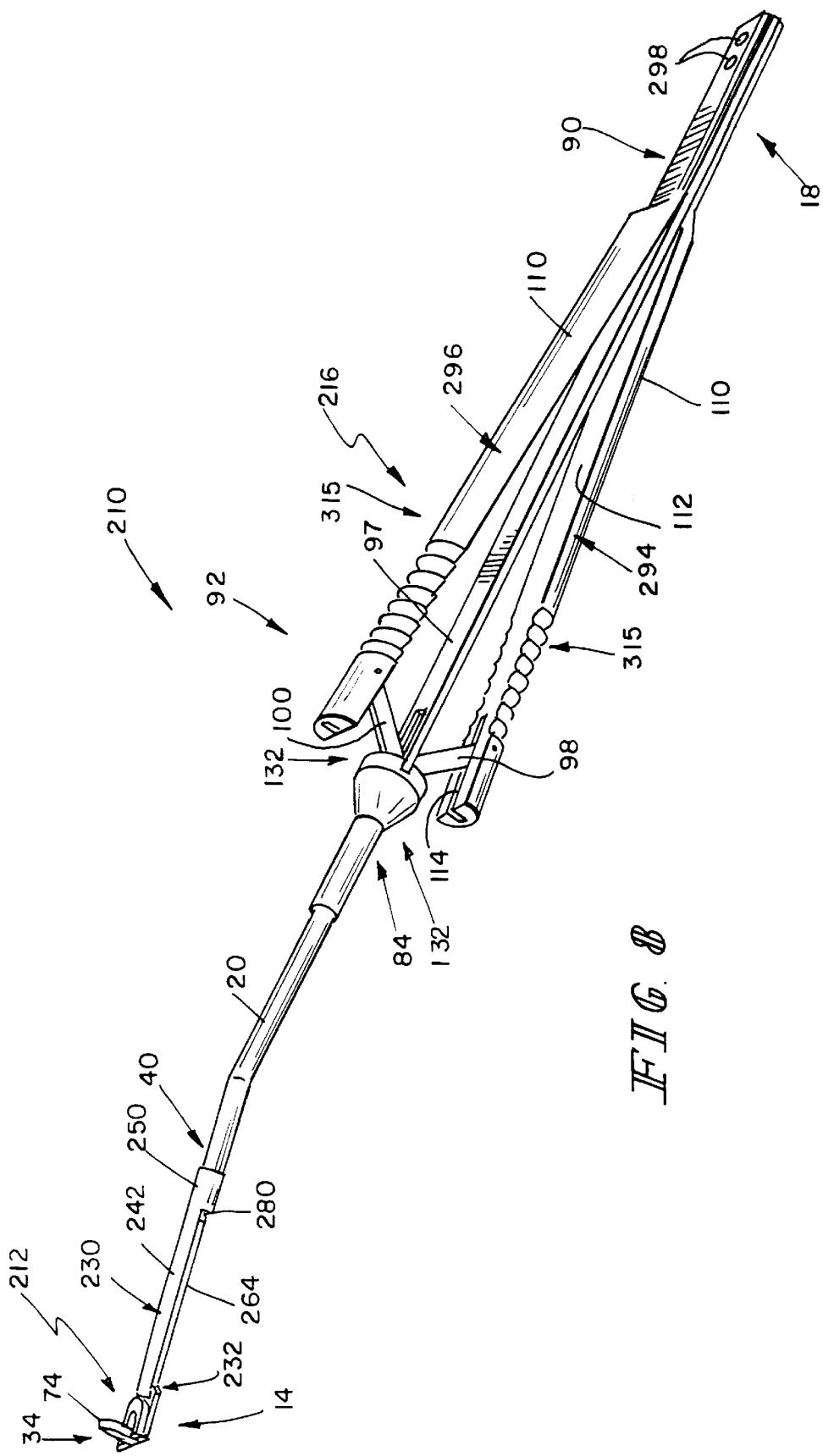
FIG. 8 is a perspective view of an alternate embodiment of the surgical instrument of the present invention showing an alternate base and slider and also showing the handle grips having a ridged portion.

Referring now to FIGS. 8–10, an alternate surgical instrument 210 is provided. Instrument 210 is formed to include a cutter 212 located at distal end 14, a handle 216 located at proximal end 18, hollow shaft 20, and a rod 22 received within hollow shaft 20. Instrument 210 is formed in a similar manner to instrument 10 and like reference numerals are used in the figures to denote like components.

Cutter 212 is formed to include an alternate base 230, an alternate slider 232, and tip 34. As shown in FIG. 9, base 230 includes proximal end 36 and distal end 38. An elongated mid-section 231 is formed to extend between proximal end 36 and distal end 38. Mid-section 231 includes a flat surface 240 and a curved surface 242. Distal end 38 of base 230 is similar to distal end 28 of base 30 wherein base 230 is formed to include two cutting edges 50 forming tear-drop shaped opening 51 extending through distal end 38 of base 230. Apertures 52 are formed to extend through distal end 38 and are provided for receiving first pin 24 in order to pivotally couple tip 34 with base 230. Proximal end 36 of base 230 is formed to include a cylindrical section 250 having a hollow portion 252 extending therethrough. Mid-section 231 also includes a cut-out portion 254, as shown (in phantom) in FIG. 9. Shaft 20 of instrument 210 is received within hollow portion 252 of base 230 similar to the manner in which shaft 20 is received within shaft-receiving aperture 47 of base 30. Base 230 operates in the same manner as base 30.

Slider 232, as shown in FIG. 10 is formed to include a distal end 260, a proximal end 262 and an elongated mid-section 264 extending between distal end 260 and proximal end 262. Mid-section 264 is formed to include a flat surface 266 and a curved surface 268 so that when cutter 212 is assembled, flat surface 266 of slider 232 is adjacent to and engaged with flat surface 240 of base 230, as shown in FIG. 8. Distal end 260 is formed to include a rectangular shaped opening 270 and apertures 70 extending through distal end 260 and provided for receiving second pin 25 in order to pivotally coupled tip 34 with slider 232. Flat surface 240 of proximal end 262 of slider 232 is formed to include a groove 274 forming a stop-surface 276. Groove 274 is formed to receive rod 22 therein so that an upper surface (not shown) of rod 22 engages stop-surface 276. Slider 232 operates in the same manner as slider 32. During operation, slider 232 is urged upward by rod 22. Opening 270 is provided to allow tissue cut from the surgical site to pass therethrough. In the fully open position, as shown in FIG. 8, a bottom surface 280 of slider 232 is positioned to rest on an upper surface 282 of cylindrical section 250 of base 230.

Handle 216 is formed to operate the same as handle 16 of instrument 10. However, a left handle grip 294 and a right handle grip 296 are provided to include a ridged portion 315 on curved outer surface 110. Similar to splined portion 115, ridged portion 315 is provided to make handle 216 easy for user 116 to grasp. Handle 216 also includes two rivets 298 shown at proximal end 18. Rivets 298 are provided in order to couple handle grips 294, 296 with center beam 97. The operation of instrument 210 is similar to the operation of instrument 10 whereby squeezing handle grips 294, 296 inward in direction 132, rod 22 is urged to move upward within shaft 20. Rod 22 thus urges slider 232 upward in order to pivot tip 34 so that cutter 212 may move from the fully open position to the fully closed position.

Surgical instruments 10, 210 are used in minimally invasive endoscopic transitional space surgeries, although either instrument 10, 210 may be used in a variety of surgeries requiring the use of a type of cutter. An initial process in most minimally invasive endoscopic transitional space surgeries is cutting an uncinate process (not shown) for the purpose of exposing an ostium (not shown), which leads into a maxillary sinus cavity (not shown) within each patient's sinuses. Either surgical instrument 10, 210 of the present invention is inserted (usually in the fully closed position) into the nasal or sinus cavity of the patient. As mentioned previously, handle 16, 216 is held by user 116 with a pencil-like grip, which is illustrated in FIG. 7. Using the pencil-like grip, surgical instrument 10, 210 may be held as shown in FIG. 7. Surgical instrument 10, 210 is inserted in the fully closed position in order to prevent cutter head 74 from catching on any sinus tissues.

Once cutter head 74 is inserted past the ostium, user 116 allows surgical instrument 10, 210 to move to the normally biased, fully open position. The surgeon or user 116 then positions surgical instrument 10, 210 so that lower surface 75 faces toward and is generally parallel with the uncinate process to be cut. Once, tip 34 is hooked just behind the uncinate process, user 116 squeezes handle grips 94, 96 or handle grips 294, 196 toward center beam 97 in a tweezer-like fashion so that cutter 12, 212 is urged to move again to the fully closed position in order to cut the uncinate process and thereby open the ostium into the maxillary sinus cavity. Although the preferred use and operation of surgical instruments 10, 210 is described above, it is within the scope of the invention to include many uses and modes of operation for surgical instruments 10, 210.

Although the invention has been described in detail with reference to certain preferred embodiments, variations and modifications exist within the scope and spirit of the invention as described and defined in the following claims.

What is claimed is:

1. A surgical instrument for cutting tissue comprising
a shaft having proximal and distal ends,
a cutter coupled to the distal end of the shaft and formed to include a base having an complimentary aperture providing two curved cutting edges, a slider positioned to lie adjacent the base, and a tip having curved cutting edges and being coupled to the base and the slider, and the cutter formed to move between a fully open position in which the curved cutting edges of the tip form an obtuse angle relative to the shaft and a fully closed position in which the tip is received within the aperture of the base, and
a handle coupled to the proximal end of the shaft and arranged to move the slider forward toward the distal end of the shaft to cause the tip to rotate counter-clockwise toward the proximal end of the shaft from the open to the closed positions.

2. The instrument of claim 1, wherein the tip is formed to include a pivot head for coupling with the base and the slider and a cutter head coupled to the pivot head.

3. The instrument of claim 2, wherein the cutter head is formed to include curved surfaces and the curved surfaces cooperate with the cutting edges of the base to form a cutting jaw.

4. The instrument of claim 2, wherein the pivot head is pivotally coupled to the base at a first pivot point and is pivotally coupled to the slider at a second pivot point generally lower than the first pivot point when the cutter is in the fully open position.

5. The instrument of claim 1, wherein the shaft is hollow and is formed to receive a rod having a distal end and a proximal end and wherein the distal end of the rod is coupled to the slider and the proximal end of the rod is coupled to the handle.

6. The instrument of claim 5, wherein the shaft remains stationary and the rod moves within the shaft as the cutter is moved from the fully open position to the fully closed position.

7. The instrument of claim 1, wherein the handle is formed to include two handle grips each having a distal end and a proximal end and wherein the proximal ends of the handle grips are coupled to each other and the distal ends of the handle grips are normally positioned to lie spaced-apart from each other.

8. The instrument of claim 7, wherein the shaft is hollow and is formed to receive a rod therein and the handle further includes a link pivotally coupled at a first end to each handle grip and pivotally coupled at a second end to the rod.

9. The instrument of claim 8, wherein the handle further includes a center beam positioned to lie between each handle grip so that as the distal ends of each handle grip are urged toward the center beam, the links urge the rod upward and wherein the rod is further coupled to the slider so that the slider is urged to move upward with the rod as each handle grip is moved toward the center beam.

10. The instrument of claim 7, wherein each handle grip is formed to include a textured pattern.

11. A surgical instrument for cutting tissue comprising
a shaft having proximal and distal ends,
a cutter coupled to the distal end of the shaft and formed to include a base having an aperture providing two cutting edges, a slider positioned to lie adjacent the base, and a tip having cutting edges and being coupled to the base and the slider, and the cutter formed to move between a fully open position in which the cutting edges of the tip form an obtuse angle relative to the shaft and a fully closed position in which the tip is received within the aperture of the base, and
a handle coupled to the proximal end of the shaft and arranged to move the tip between the open and closed positions, and
wherein the slider is formed to include an aperture through which cut tissue may pass.

12. The instrument of claim 11, wherein the aperture of the slider is aligned with the aperture of the base when the cutter is in the fully closed position.

13. The instrument of claim 11, wherein the tip is formed to include a pivot head for coupling with base and slider an a cutter head coupled to the pivot head.

14. The instrument of claim 13, wherein the cutter head is formed to include curved surfaces and wherein the curved surfaces cooperate with the cutting edges of the base to form a cutting jaw.

15. The instrument of claim 13, wherein the pivot head is pivotally coupled to the base at a first pivot point and is pivotally coupled to the slider at a second pivot point generally lower than the first pivot point when the cutter is in the fully open position.

16. The instrument of claim 11, wherein the shaft is hollow and is formed to receive a rod having a distal end and a proximal end and wherein the distal end of the rod is coupled to the slider and the proximal end of the rod is coupled to the handle.

17. The instrument of claim 16, wherein the shaft remains stationary and the rod moves within the shaft as the cutter is moved from the fully open position to the fully closed position.

18. The instrument of claim 11, wherein the handle is formed to include two handle grips each having a distal end and a proximal end and wherein the proximal ends of the handle grips are coupled to each other and the distal ends of the handle grips are normally positioned to lie spaced-apart from each other.

19. The instrument of claim 18, wherein the shaft is hollow and is formed to receive a rod therein and the handle further includes a link pivotally coupled at a first end to each handle grip and pivotally coupled at a second end to the rod.

20. The instrument of claim 19, wherein the handle further includes a center beam positioned to lie between each handle grip so that as the distal ends of each handle grip are urged toward the center beam, the links urge the rod upward and wherein the rod is further coupled to the slider so that the slider is urged to move upward with the rod as each handle grip is moved toward the center beam.

21. The instrument of claim 18, wherein each handle grip is formed to include a textured pattern.

22. A surgical instrument for cutting tissue and positioned to engage an index finger and a thumb and to be supported by a middle finger of a surgeon or user when cutting tissue, the surgical instrument comprising
   a shaft having proximal and distal ends,
   a rod movable relative to the shaft,
   a cutter coupled to the distal end of the shaft and formed to include a cutter blade having two curved cutting surfaces, a base having two oppositely curved edges forming an opening adapted to cooperate with the cutting surfaces of the cutter blade in order to cut tissue, and a slider coupled to the rod and the cutter blade and also having an opening through which the cut tissue may pass, and
   a handle coupled to the shaft and the rod and arranged to move the rod relative to the shaft in order to move the cutter blade to a position received within the opening of the base.

23. The instrument of claim 13, wherein the cutter blade further includes an upper surface and a lower surface and the cutter is formed to move between a fully open position in which the lower surface of the cutter blade and the distal end of the shaft form an obtuse angle and a fully closed position in which the cutter blade is received within the opening of the base.

24. The instrument of claim 22, wherein the handle includes a right handle grip, a left handle grip, a center beam positioned to lie between the right and left handle grips, and a link coupled to each handle grip at a first pivot point and the rod at a second pivot point.

25. The instrument of claim 24, wherein the right handle grip, left handle grip, and center beam are coupled to each other at a proximal end and are spaced-apart from each other at an opposite distal end when the cutter is in the fully open position.

26. The instrument of claims 25, wherein the right handle grip and the left handle grip are adjacent to and in engagement with the center beam when the cutter is in the fully closed position.

27. The instrument of claim 24, wherein the right and left handle grips are each formed to include a ridged portion.

28. The instrument of claim 24, wherein the cutter blade is pivotally coupled to the slider and as the right and left handle grips are squeezed together, the links urge the rod and slider to move upward causing the cutter blade to pivot about the slider and toward the base.

29. The instrument of claim 22, wherein the cutter blade is coupled to the base at a first pivot point and the cutter blade is coupled to the slider at a second pivot point normally positioned to lie generally below the first pivot point.

30. The instrument of claim 29, wherein the second pivot point is positioned to lie generally above the first pivot point when the cutter blade is received within the opening of the base.

31. The instrument of claim 22, wherein the cutter blade further includes an upper surface and a lower surface, and wherein the lower surface is formed to include a hollowed-out portion.

32. A surgical instrument to be operated by the thumb and index finger, the surgical instrument comprising
   a shaft having a distal end, a proximal end, and an axis extending between distal and proximal ends,
   a rod received within the shaft and formed to include a distal end and a proximal end,
   a cutter including a cutter head, a base having a top surface, a bottom surface, and side walls extending therebetween and being coupled to the distal end of the shaft, and a slider having a top surface, a bottom surface, and side walls extending therebetween and being coupled to the distal end of the rod so that the top surface of the slider normally engages the bottom surface of the base, and
   a drive assembly coupled to the proximal end of the rod and the shaft and the cutter and movable between open and closed positions wherein movement of the rod past the proximal end of the shaft causes movement of the drive assembly between the open and closed positions as it rotates the cutter counter-clockwise toward the distal end of the shaft about a generally transverse axis to the axis of the shaft.

33. The instrument of claim 32, wherein the cutter head is formed to include two curved cutting surfaces adapted to cut tissue.

34. The instrument of claim 33, wherein the cutter head further includes a bottom surface having a hollowed-out portion formed therein.

35. The instrument of claim 33, wherein the base is formed to include two curved cutting edges for cooperation with the curved cutting surfaces of the cutter head in order to produce a shearing motion between the cutting edges and the cutting surfaces.

36. The instrument of claim 32, wherein the base further includes two cutting edges forming an aperture and the cutter head is received within the aperture when the drive assembly is in the closed position.

37. The instrument of claim 32, wherein the drive assembly is formed to include a right handle grip, a left handle grip, and a center beam positioned to lie between the right and left handle grips.

38. The instrument of claim 37, wherein the right handle grip, left handle grip, and center beam are coupled to each other at a proximal end and are spaced-apart from each other at an opposite distal end when the drive assembly is in the open position.

39. The instrument of claim 37, wherein the right handle grip and the left handle grip are each coupled to the center beam at a distal end and are positioned to lie adjacent to and engaged with the center beam at a proximal end when the drive assembly is in the closed position.

40. The instrument of claim 37, wherein the drive assembly further includes a link pivotally coupled at a first end to each of the right and left handle grips and pivotally coupled at a second end to the rod.

41. The instrument of claim 40, wherein the shaft is coupled to the center beam and the rod is moved relative to the shaft as the drive assembly is moved between open and closed positions.

42. A surgical instrument to be operated by the thumb and index finger, the surgical instrument comprising a shaft having a distal end, a proximal end, and an axis extending between distal and proximal ends, a rod received within the shaft and formed to include a distal end and a proximal end, a cutter including a cutter head, a base having a top surface, a bottom surface, and side walls extending therebetween and being coupled to the distal end of the shaft, and a slider having a top surface, a bottom surface, and side walls extending therebetween and being coupled to the distal end of the rod so that the top surface of the slider normally engages the bottom surface of the base, and a drive assembly coupled to the proximal end of the rod and the shaft and movable between open and closed positions wherein the direction of movement of the drive assembly between the open and closed positions is generally transverse to the axis of the shaft, wherein the base further includes two cutting edges forming an aperture and the cutter head is received within the aperture when the drive assembly is in the closed position, and wherein the slider is formed to include an opening such that the opening aligns with the aperture of the base when the drive assembly is in the closed position.

43. The instrument of claim 42, wherein the cutter head is formed to include two curved cutting surfaces adapted to cut tissue.

44. The instrument of claim 43, wherein the cutter head further includes a bottom surface having a hollowed-out portion formed therein.

45. The instrument of claim 43, wherein the base is formed to include two curved cutting edges for cooperation with the curved cutting surfaces of the cutter head in order to produce a shearing motion between the cutting edges and the cutting surfaces.

46. The instrument of claim 42, wherein the drive assembly is formed to include a right handle grip, a left handle grip, and a center beam positioned to lie between the right and left handle grips.

47. The instrument of claim 46, wherein the right handle grip, left handle grip, and center beam are coupled to each other at a proximal end and are spaced-apart from each other at an opposite distal end when the drive assembly is in the open position.

48. The instrument of claim 46, wherein the right handle grip and the left handle grip are each coupled to the center beam at a distal end and are positioned to lie adjacent to and engaged with the center beam at a proximal end when the drive assembly is in the closed position.

49. The instrument of claim 46, wherein the drive assembly further includes a link pivotally coupled at a first end to each of the right and left handle grips and pivotally coupled at a second end to the rod.

50. The instrument of claim 49, wherein the shaft is coupled to the center beam and the rod is moved relative to the shaft as the drive assembly is moved between open and closed positions.

* * * * *